US012446962B2

(12) United States Patent
Rozen

(10) Patent No.: US 12,446,962 B2
(45) Date of Patent: Oct. 21, 2025

(54) SPINE STRESS MAP CREATION WITH FINITE ELEMENT ANALYSIS

(71) Applicant: Mazor Robotics Ltd., Caesarea (IL)

(72) Inventor: Rakefet Rozen, Balfouria (IL)

(73) Assignee: Mazor Robotics Ltd., Caesarea (IL)

( * ) Notice: Subject to any disclaimer, the term of this patent is extended or adjusted under 35 U.S.C. 154(b) by 419 days.

(21) Appl. No.: 17/988,019

(22) Filed: Nov. 16, 2022

(65) Prior Publication Data

US 2024/0156529 A1 May 16, 2024

(51) Int. Cl.
*A61B 34/10* (2016.01)
*G06T 7/10* (2017.01)

(52) U.S. Cl.
CPC ................ *A61B 34/10* (2016.02); *G06T 7/10* (2017.01); *A61B 2034/105* (2016.02); *A61B 2034/107* (2016.02); *G06T 2207/10088* (2013.01); *G06T 2207/20081* (2013.01); *G06T 2207/30012* (2013.01)

(58) Field of Classification Search
CPC .............. A61B 34/10; A61B 2034/105; A61B 2034/107; G06T 2207/10088; G06T 2207/20081; G06T 2207/30012; G06T 7/10
See application file for complete search history.

(56) References Cited

U.S. PATENT DOCUMENTS

| | | | | |
|---|---|---|---|---|
| 8,098,543 B2 * | 1/2012 | Bachrach | ................. | G01V 1/30 367/73 |
| 8,285,364 B2 * | 10/2012 | Barbagli | .................. | A61B 5/06 600/459 |
| 10,102,626 B2 * | 10/2018 | Chou | ................. | G01R 33/4808 |
| 10,748,451 B2 * | 8/2020 | Randles | .................... | G06T 7/11 |

(Continued)

FOREIGN PATENT DOCUMENTS

| | | |
|---|---|---|
| CN | 111460707 | 7/2020 |
| WO | WO 2022/192222 | 9/2022 |

OTHER PUBLICATIONS

Galbusera et al. "Planning the surgical correction of spinal deformities: toward the identification of the biomechanical principles by means of numerical simulation," Frontiers in Bioengineering and Biotechnology, Nov. 2015, vol. 3, Article 178, 14 pages.

(Continued)

*Primary Examiner* — Gregory M Desire
(74) *Attorney, Agent, or Firm* — Sheridan Ross P.C.

(57) ABSTRACT

A system and techniques for creating a spine stress map are provided. The system may be configured to generate a multi-class segmentation for an anatomical element of a patient based on a plurality of magnetic resonance images of the anatomical element from a plurality of patients. Additionally, one or more stress maps may be generated based on simulating stresses on the anatomical element. In some embodiments, the simulated stresses may be simulated using (Continued)

a finite element analysis based at least in part on the multi-class segmentation. Additionally, the system may be configured to display one or more stress maps via a user interface, where the one or more stress maps are determined based on one or more deep learning models configured to predict multi-labeled masks and/or stress maps for the anatomical element.

18 Claims, 6 Drawing Sheets

(56) References Cited

U.S. PATENT DOCUMENTS

| | | | | |
|---|---|---|---|---|
| 10,922,816 | B2 * | 2/2021 | Huang | G16H 30/40 |
| 11,164,285 | B2 * | 11/2021 | Kim | G06T 7/246 |
| 11,207,135 | B2 * | 12/2021 | Schmidt | G16H 50/50 |
| 11,883,219 | B2 * | 1/2024 | Boddington | G06T 7/30 |
| 2019/0290361 | A1 | 9/2019 | Shalayev et al. | |
| 2020/0078180 | A1 | 3/2020 | Casey | |
| 2020/0373013 | A1 | 11/2020 | Cao et al. | |
| 2021/0193326 | A1 * | 6/2021 | Kim | G16H 50/50 |

OTHER PUBLICATIONS

Talukdar et al. "Numerical analysis of the mechanical behaviour of intact and implanted lumbar functional spinal units: Effects of loading and boundary conditions," Proceedings of the Institution of Mechanical Engineers, Journal of Engineering in Medicine, Part H. May 2021, vol. 235, No. 7, pp. 792-804.

International Search Report for International (PCT) Patent Application No. PCT/IL2023/051166, dated Mar. 14, 2024.

* cited by examiner

SPINE STRESS MAP CREATION WITH FINITE ELEMENT ANALYSIS

BACKGROUND

The present disclosure is generally directed to spine stress maps, and relates more particularly to using finite element (FE) analysis to create spine stress maps.

Spine stenoses conditions are caused when stress is applied on the spinal cord of a patient and frequently causes pain to the patient. Additionally, spine stenosis is a common reason for back surgery of patients. For example, a patient may undergo a laminectomy, which comprises a surgery that creates space by removing bone spurs and tissues of the spine. Laminectomies usually involve removing a small piece of the back part (e.g., lamina) of the small bones of the spine (e.g., vertebrae), which may enlarge the spinal canal to relieve pressure and stress on the spinal cord or nerves. Additionally or alternatively, a patient may undergo a laminotomy, which comprises a less invasive surgery where a smaller incision is made to remove a smaller piece of the back part of the small bones of the spine than removed in laminectomies. In some cases, back surgeries may benefit from the use of spine stress maps to identify specific areas of the spine that experience higher amounts of stress for more targeted and effective surgeries.

BRIEF SUMMARY

Example Aspects of the Present Disclosure Include:

A system for creating a spine stress map, comprising: a processor; and a memory storing data for processing by the processor, the data, when processed, causes the processor to: generate a multi-class segmentation for an anatomical element of a patient based at least in part on a plurality of magnetic resonance images of the anatomical element from a plurality of patients; generate a plurality of stress maps based at least in part on simulating stresses on the anatomical element, the simulated stresses being simulated using a finite element analysis based at least in part on the multi-class segmentation; determine one or more stress maps of the plurality of stress maps to display based at least in part on one or more deep learning models configured to predict multi-labeled masks and/or stress maps for the anatomical element; and display the one or more stress maps via a user interface.

Any of the aspects herein, wherein the memory stores further data for processing by the processor that, when processed, causes the processor to: train a deep learning model based at least in part on the plurality of magnetic resonance images of the anatomical element from the plurality of patients; and generate the multi-class segmentation based at least in part on the deep learning model.

Any of the aspects herein, wherein the deep learning model is further trained based at least in part on a plurality of annotated soft tissue segmentation maps for the anatomical element from the plurality of patients.

Any of the aspects herein, wherein the plurality of magnetic resonance images comprises a plurality of three-dimensional magnetic resonance images.

Any of the aspects herein, wherein the memory stores further data for processing by the processor that, when processed, causes the processor to: simulate a plurality of stresses on the anatomical element based at least in part on simulating a plurality of physiological movements and deformations that cause stress on the anatomical element.

Any of the aspects herein, wherein the memory stores further data for processing by the processor that, when processed, causes the processor to: generate individual stress maps for each of the plurality of simulated stresses, wherein the plurality of stress maps comprises the individual stress maps.

Any of the aspects herein, wherein the memory stores further data for processing by the processor that, when processed, causes the processor to: train a deep learning model based at least in part on the plurality of stress maps and the multi-class segmentation for the anatomical element; and generate the one or more stress maps to display via the user interface based at least in part on the deep learning model.

Any of the aspects herein, wherein the memory stores further data for processing by the processor that, when processed, causes the processor to: generate a plurality of simulated stress relief maps based at least in part on the plurality of stress maps and simulating removal of one or more portions of the anatomical element, wherein the one or more portions of the anatomical element are simulated being removed based at least in part on an additional finite element analysis; and display, via the user interface, a suggested surgical plan generated based at least in part on the plurality of simulated stress relief maps.

Any of the aspects herein, wherein the memory stores further data for processing by the processor that, when processed, causes the processor to: train a deep learning model based at least in part on the plurality of simulated stress relief maps, wherein the suggested surgical plan is generated based at least in part on the deep learning model.

Any of the aspects herein, wherein the plurality of stress maps comprises three-dimensional stress maps of the anatomical element.

A system for creating a spine stress map, comprising: a processor; and a memory storing data for processing by the processor, the data, when processed, causes the processor to: generate a multi-class segmentation for an anatomical element of a patient based at least in part on a plurality of magnetic resonance images of an anatomical element from a plurality of patients; generate a plurality of stress maps for the anatomical element of a patient based at least in part on simulating stresses on the multi-class segmentation of the anatomical element, the simulated stresses being simulated using a finite element analysis based at least in part on the multi-class segmentation; determine one or more stress maps of the plurality of stress maps to display based at least in part on a deep learning model configured to predict multi-labeled masks and/or stress maps for the anatomical element; and display one or more of the plurality of stress maps via a user interface.

Any of the aspects herein, wherein the memory stores further data for processing by the processor that, when processed, causes the processor to: train a first deep learning model based at least in part on the plurality of magnetic resonance images of the anatomical element from the plurality of patients; and generate the multi-class segmentation based at least in part on the first deep learning model.

Any of the aspects herein, wherein the memory stores further data for processing by the processor that, when processed, causes the processor to: train a second deep learning model based at least in part on the plurality of stress maps and the multi-class segmentation for the anatomical element; and generate the one or more of the plurality of stress maps to display via the user interface based at least in part on the deep learning model.

Any of the aspects herein, wherein the first deep learning model is further trained based at least in part on a plurality of annotated soft tissue segmentation maps for the anatomical element from the plurality of patients.

Any of the aspects herein, wherein the memory stores further data for processing by the processor that, when processed, causes the processor to: simulate a plurality of stresses on the anatomical element based at least in part on simulating a plurality of physiological movements and deformations that cause stress on the anatomical element.

Any of the aspects herein, wherein the memory stores further data for processing by the processor that, when processed, causes the processor to: generate individual stress maps for each of the plurality of simulated stresses, wherein the plurality of stress maps comprises the individual stress maps.

Any of the aspects herein, wherein the memory stores further data for processing by the processor that, when processed, causes the processor to: generate a plurality of simulated stress relief maps based at least in part on the plurality of stress maps and simulating removal of one or more portions of the anatomical element, wherein the one or more portions of the anatomical element are simulated being removed based at least in part on an additional finite element analysis; and display, via the user interface, a suggested surgical plan generated based at least in part on the plurality of simulated stress relief maps.

Any of the aspects herein, wherein the memory stores further data for processing by the processor that, when processed, causes the processor to: train a deep learning model based at least in part on the plurality of simulated stress relief maps, wherein the suggested surgical plan is generated based at least in part on the deep learning model.

A system for creating a spine stress map, comprising: a processor; and a memory storing data for processing by the processor, the data, when processed, causes the processor to: generate a plurality of stress maps and a multi-class segmentation for a spinal cord of a patient based at least in part on simulating stresses on the spinal cord, the simulated stresses being simulated using a finite element analysis based at least in part on the multi-class segmentation; determine one or more stress maps of the plurality of stress maps to display based at least in part on one or more deep learning models configured to predict multi-labeled masks and/or stress maps for the spinal cord; and display one or more of the plurality of stress maps via a user interface.

Any of the aspects herein, wherein the simulated stresses comprise moving a vertebra of the spinal cord, squeezing a disc of the spinal cord, resizing a ligamentum flavum of the spinal cord, a deformation of the spinal cord, an additional physiological movement of the spinal cord, or a combination thereof.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
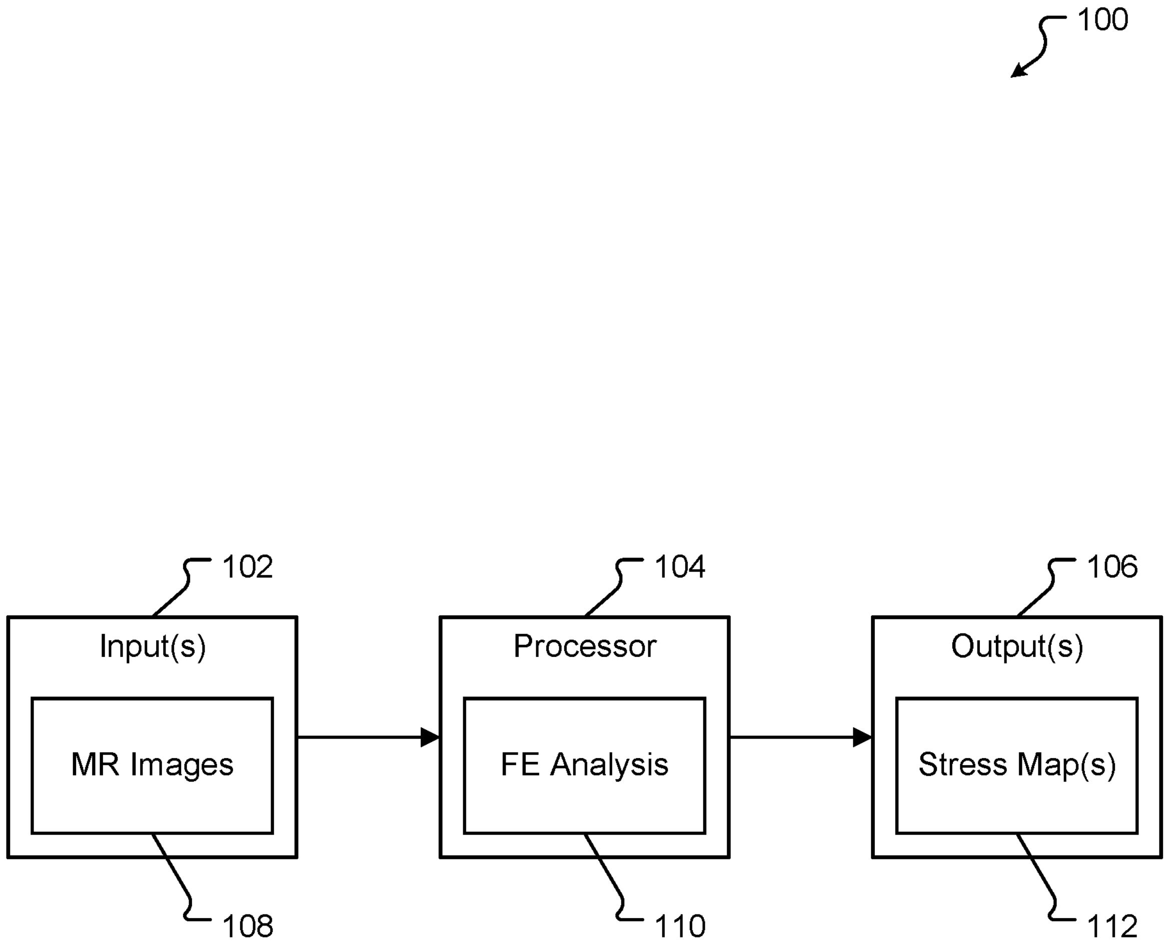
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10× Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Spine stenoses conditions are caused when stress is applied on the spinal cord of a patient and frequently causes pain to the patient. Additionally, spine stenosis is a common reason for back surgery of patients. As described herein, the spine may comprise a number of vertebrae (e.g., typically 33 vertebrae), a number of intervertebral discs (e.g., typically 23 intervertebral discs, which are pads located between the vertebrae), the spinal cord, and connecting ribs. For example, a patient may undergo a laminectomy, which comprises a surgery that creates space by removing bone spurs and tissues of the spine. Laminectomies usually involve removing a small piece of the back part (e.g., lamina) of the small bones of the spine (e.g., vertebrae), which may enlarge the spinal canal to relieve pressure and stress on the spinal cord or nerves. Additionally or alternatively, a patient may undergo a laminotomy, which comprises a less invasive surgery where a smaller incision is made to remove a smaller piece of the back part of the small bones of the spine than removed in laminectomies.

In order to perform minimal invasive surgery, a surgeon may identify the stressed areas of the patient. Accordingly, to perform a spine surgery (e.g., for stress release) and identify the stressed areas, a surgeon would benefit if a magnetic resonance (MR) image (e.g., of the patient's spine) included a three-dimensional (3D) stress map of the spine. The stress map may help the surgeon perform minimal and accurate bone cutting by identifying the bone parts to be removed that are creating the stress on the nerve (e.g., "pushing the nerve"). That is, back surgeries may benefit from the use of spine stress maps that identify specific areas of the spine that experience higher amounts of stress for more targeted and effective surgeries.

As described herein, techniques are provided for creating spine stress maps based on a combination of finite element (FE) analysis and deep learning models. For example, the spine stress maps may be created based on one or more deep learning models and an FE analysis. A first deep learning model is trained based on a plurality of 3D MR images of spines of previous patients (e.g., an MR imaging (MM) spine database) and configured to create a 3D multi-class segmentation of a current patient's spine. The 3D multi-class segmentation is then used as an input into the FE analysis which simulates a plurality of stresses for the patient's spine (e.g., physiological movements, deformations, and/or material changes, such as degeneration of a disc, that may cause stenosis) and creates a stress map for each simulation. The simulation end results may be generated based on the first deep learning model trained using the plurality of 3D MR images of spines, such that the spine stress maps are predicted from real images (e.g., the 3D MR images of spines) and not simulated images. Based on the FE analysis, each simulation end result may be saved as a segmentation map with a corresponding stress map.

A second deep learning model may then take the simulation end results (e.g., segmentation maps and stress maps) as an input to generate a cumulative stress map for the patient that is displayed (e.g., via a user interface) for the surgeon to identify the stressed areas of the patient's spine for performing surgery. In some embodiments, from an MR image, the first deep learning model may predict one or more multi-labeled masks, and from the multi-labeled mask(s), the second deep learning model may predict stress maps. Additionally, the second deep learning model may also generate a recommendation or suggestion for a stress release bone cut for the surgeon to make (e.g., bone cut suggestion map), which can be also displayed for the surgeon to view.

The spine stress maps can aid the surgeon with identifying minimal bone areas to cut off for creating stress release. Additionally, the described techniques can reduce the amount of bone removal and reduce future pain from the patient. In some embodiments, the spine stress maps may help to avoid surgeries as laminectomies and favor laminotomies. The laminotomies can be fine-tuned by the spine stress maps so that only bones adjacent to a stressed nerve will be removed. Additionally, the bone cut suggestion may set a best minimal bone cut and stress release for the surgeon.

FIG. 1 is a block diagram of a system 100 according to at least one embodiment of the present disclosure. The system 100 may include one or more inputs 102 that are used by a processor 104 to generate one or more outputs 106. The processor 104 may be part of a computing device or different device. Additionally, the processor 104 may be any processor described herein or any similar processor. The processor 104 may be configured to execute instructions or data stored in a memory, which the instructions or data may cause the processor 104 to carry out one or more computing steps utilizing or based on the inputs 102 to generate the outputs 106.

As described herein, the inputs 102 may include one or more MR images 108. For example, the MR images 108 may comprise a plurality of 3D MR images of spines from previous patients that may or may not have undergone spine surgeries to relieve stress on their spines (e.g., an MRI spine database). In some examples, the MR images 108 may include MR images of spines that are considered "good" or healthy (e.g., spines of patients that do not have stenosis and/or experience other types of back pain) and spines that are injured or unhealthy (e.g., spines of patients that do have stenosis and/or experience other types of back pain). For example, the "good" spines may include spines that are considered well (e.g., not in pain or hurt) and/or spines of patients that are in pain or hurt but the pain is present in parts of the spine (e.g., vertebras) not in pain for the given patient (e.g., not the vertebras or areas that are in pain for the given patient).

In some embodiments, the processor 104 may take the inputs 102, such as the MR images 108 of "good" spines, to find differences (e.g., deltas) between the "good" spines and degenerative simulations for a given patient's spine and may run stress simulations on the given patient's spine to identify the differences. For example, the processor 104 may perform an FE analysis 110 to mimic a "degenerative spine" representative of the given patient based on simulating different deformations and/or degenerative conditions and then simulate different stresses on the "degenerative spine" to identify the differences. As part of the FE analysis 110, parameters for each element of the patient's spine can be entered (e.g., based on differences between the given patient's spine and the "good" spines). For example, the parameters may include a plurality of parameters for each element of the spine (e.g., discs, vertebras, canals, ligaments, etc.), such as an elasticity, rigidity, mimicking different amounts of hydrogen, size, thickness, and/or other parameters that characterize each element of the spine. In some examples, the parameters for each element may be determined or adjusted based on scans of the given patient's spine previously taken (e.g., computerized tomography (CT) scans).

After the different parameters for each element of the given patient's spine are entered for the FE analysis 110, the FE analysis 110 may then comprise simulating different stresses on the "degenerative spine" or model representing the given patient's spine. For example, the simulations may include physiological movements and deformations that can potentially cause stenosis on the given patient's spine, such as, but not limited to, moving a vertebra, squeezing a disc, resizing the ligamentum flavum (e.g., ligaments that connect the ventral parts or nerves of the laminae of adjacent vertebrae), etc.

Based on the simulated stresses (e.g., generated in part based on one or more deep learning models as described with reference to FIG. 2 along with the FE analysis 110), the FE analysis 110 may generate one or more stress maps 112 as the outputs 106 of the system 100. For example, a segmentation map with a corresponding stress map may be produced for each simulation end result (e.g., each simulated stress). In some embodiments, the stress maps 112 may be compiled to create or predict a single stress map for the given patient's spine to determine which areas of the given patient's spine could experience the highest amount of stress and be targets for surgery. The stress maps 112 and/or single stress map may be displayed (e.g., via a user interface) for the surgeon to view and plan the surgery accordingly to relieve the predicted stress(es).

Additionally or alternatively, the FE analysis 110 may be used to generate a recommendation of a stress release bone cut for the surgeon to make (e.g., a bone cut suggestion or recommendation), which can also be displayed (e.g., via the user interface). For example, as part of the FE analysis 110 after the different stresses have been simulated, different surgery simulations may also be performed to identify which surgery has the highest chance of relieving the simulated stresses. That is, the different surgery simulations may comprise simulations of removing different portions of the spine (e.g., as part of a laminotomy), and the bone cut suggestion or recommendation may be generated based on which of the different surgery simulations results in relieving the simulated stresses on the given patient's spine.

As described herein, in addition to the FE analysis 110, the processor 104 may employ one or more deep learning models (e.g., artificial intelligence (AI) models), neural networks, etc.) to generate the stress maps 112 as the output(s) 106 of the system 100 based on the MR images 108 and/or other input(s) 102 for the system 100. The deep learning model(s) are described in greater detail with reference to FIG. 2.

Figure 2:
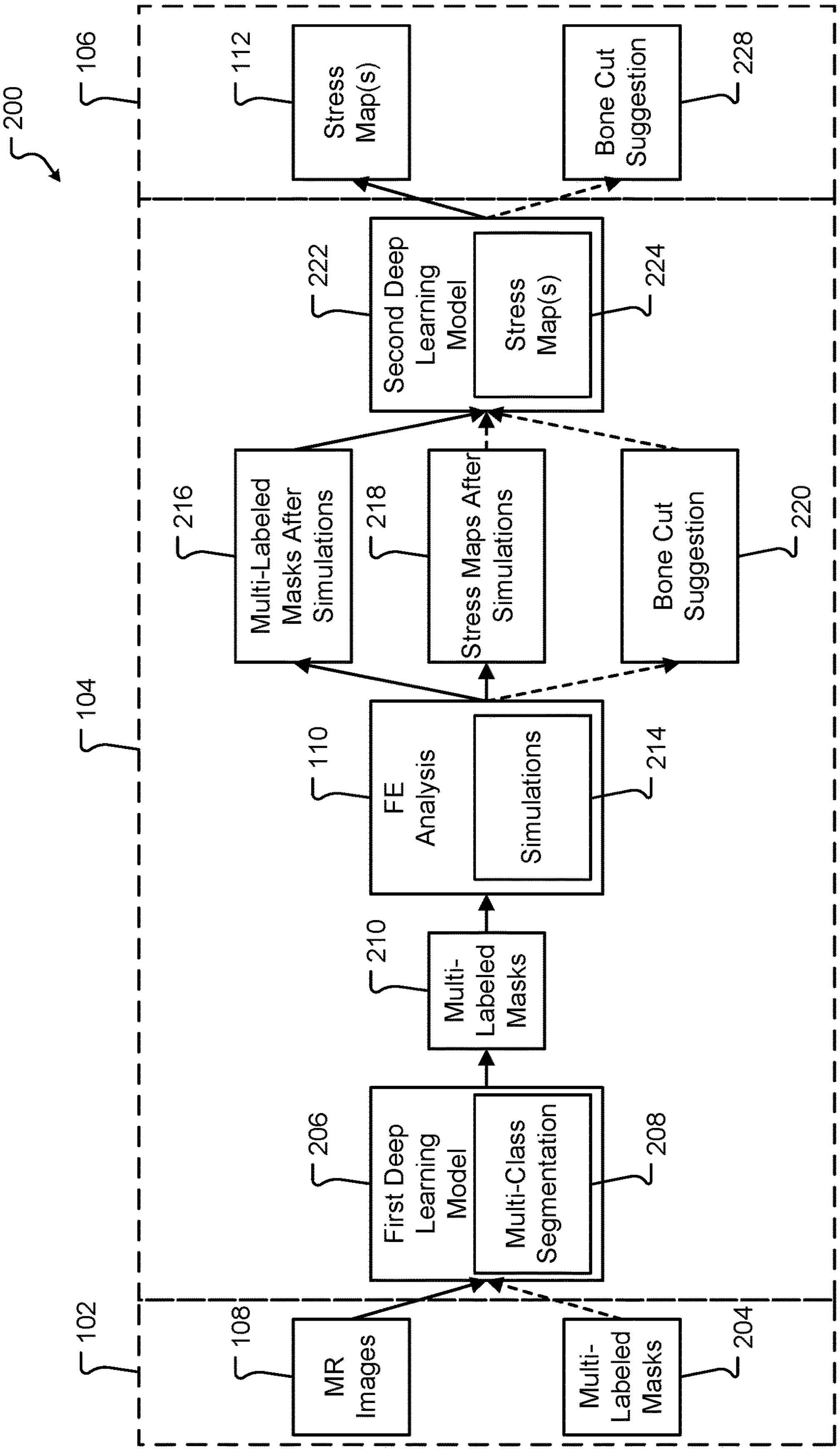
FIG. 2 is a diagram of a training flow according to at least one embodiment of the present disclosure.

FIG. 2 is a diagram of a training flow 200 according to at least one embodiment of the present disclosure. In some examples, the training flow 200 may implement aspects of or may be implemented by aspects of FIG. 1. For example, the training flow 200 may be a more detailed view of the system 100, where a plurality of MR images 108 are used, in part, as inputs 102 to carry out one or more computing steps of a processor 104 (e.g., including an FE analysis 110) to generate output 106, including stress maps 112.

As described previously with reference to FIG. 1, the plurality of MR images 108 (e.g., 3D MR images) may be used as an input 102 for the training flow 200, where the plurality of MR images 108 comprise MR images of spines (e.g., an MRI spine database of spines of patients). For example, the MR images 108 may comprise MR images of "good" spines (e.g., spines of patients that are not experiencing pain or are experiencing pain in areas of their spines not being experienced by a current patient) and "bad" spines (e.g., spines of patients that have stenosis and/or experience other types of back pain). Additionally, the inputs 102 may include multi-labeled masks 204 (e.g., 3D MR multi-labeled masks) of spines. For example, the multi-labeled masks 204 may include labeled or annotated images (e.g., masks) of segmentations that collectively cover the entirety of a spine, indicating the different elements of the spine (e.g., discs, vertebras, canals, ligaments, etc.).

The MR images 108 and the multi-labeled masks 204 may be used to train a first deep learning model 206 (e.g., Model1) that takes the 3D MRIs (e.g., MR images 108) to generate a multi-class segmentation 208 (e.g., 3D multi-class segmentation) for a given patient's spine. For example, the first deep learning model 206 may be trained based at least in part on inputs from an MRI spine database (e.g., MR images 108) and annotated soft tissue segmentation maps (e.g., multi-labeled masks 204) that include all soft and bony elements of the patient's spine to create a 3D multi-class segmentation (e.g., 3D multi-segmentation mask, 3D multi-labeled masks, etc.) as an inference or output. That is, the first deep learning model 206 may take one or more MR images and create a classification to sub anatomical elements of a patient's spine and mask the elements to create a mesh of each element, such as the canal, the vertebrae, the discs, etc. Additionally, based on being trained using the MR images 108 that comprise MR images of both "good" and "bad" spines, the first deep learning model 206 may be configured to segment any type of spine. In some examples, the elements may have different classes. Additionally, the first deep learning model 206 may output multi-labeled masks 210.

Subsequently, the FE analysis 110 may create a simulated stenosis for the given patient's spine out of the multi-labeled masks 210 (e.g., 3D masks output of the first deep learning model 206) that results in a stress map. For example, the FE analysis 110 may run a plurality of simulations 214 that include physiological movements and deformations that may cause stenosis for the given patient. In some examples, in the FE analysis 110, "good" candidates (e.g., MR images of patients with "good" spines) may be used to simulate the deformations and/or degenerative simulations for the given patient. The simulations 214 may include, but are not limited to, moving one or more vertebrae, squeezing a disc, resizing the ligamentum flavum (e.g., thicker ligamentum flavum may push the canal to cause stenosis), classifications of a degenerative element, etc. In some embodiments, the FE analysis 110 may create stress maps (e.g., von mises stress maps) for each simulation and may save each simulation end result as a segmentation map with a corresponding stress map. For example, the FE analysis 110 may create one or more multi-labeled masks 216 after each simulation and corresponding stress maps 218 after each simulation (e.g., the stress maps 218 may comprise a regression model that predicts a continuous value). In some embodiments, the FE analysis 110 may also save a recommendation of a stress release bone cut based on the simulations (e.g., a bone cut suggestion 220).

That is, results of the first deep learning model 206 are input into the FE analysis 110, which takes the labeled elements (e.g., masks) and performs different simulations 214 that create and mimic a degenerative back. Each element of the spine (e.g., disc, vertebra, canal, etc.) is assigned specific parameters, such as an elasticity, rigidity, or additional parameters that characterize the element. As an example, the FE analysis 110 may take a disc and change and characterize the soft tissue of the disc from parameters of the material itself (e.g., based on parameters for a disc of the given patient's spine, such as acquired from CT scans for the patient), such as simulating the disc is harder based on having less hydrogen or less liquid. Accordingly, the FE analysis 110 may change the parameters of the disc (e.g., or other element of the spine) as a simulation and determines what would happen to the surrounding elements of the spine (e.g., a vertebra on top of the disc and a vertebra below the disc) and the stresses that this change creates as a result. Additionally or alternatively, the FE analysis may simulate a break in one or more of the elements of the spine (e.g., such as a vertebra fracture) determine what stresses are created based on the fracture or break. Accordingly, the FE analysis 110 may create the stress maps 218 based on the different simulations 214. In some embodiments, the simulations 214 may be performed based on differences or deltas between a patient's current or initial condition and simulated deformations for the patient's spine based in part on the "good" spines included in the MR images 108.

The processor 104 may then employ a second deep learning model 222 (e.g., Model2) that takes a 3D multi-class segmentation (e.g., at the end of the simulations 214) to generate one or more stress maps 224 (e.g., 3D stress maps) and optionally a bone cut suggestion map (e.g., bone cut suggestion 228). For example, the second deep learning model 222 may be trained using the outputs of the FE analysis 110, such as end of simulation multi-labeled segmentation masks 216 and the stress maps 218 to predict stress maps 224 and optionally the bone cut suggestion 228 (e.g., 3D bone cut suggestion) from a multi segmentation 3D image. In some embodiments, an inference of the second deep learning model 222 may include predicting, from the multi-labeled masks 216 (e.g., 3D multi-class segmentation), a stress map 224 and/or stress map 112 and optionally the bone cut suggestion 228.

That is, the multi-labeled masks 216 and the stress maps 218 generated from the FE analysis 110 are used to teach or train the second deep learning model 222, and the second deep learning model 222 may be configured to generate an inference comprising the stress map 224. For example, the second deep learning model 222 may generate stress maps based on differences between degenerative backs and "good" backs. Accordingly any given patient's spine may be input into the processor 104 (e.g., employing the first deep learning model 206, the FE analysis 110, and the second deep learning model 222) to identify differences (e.g., deltas) in the given patient's spine from a "good" back and generate stress maps for the given patient's spine.

Figure 3:
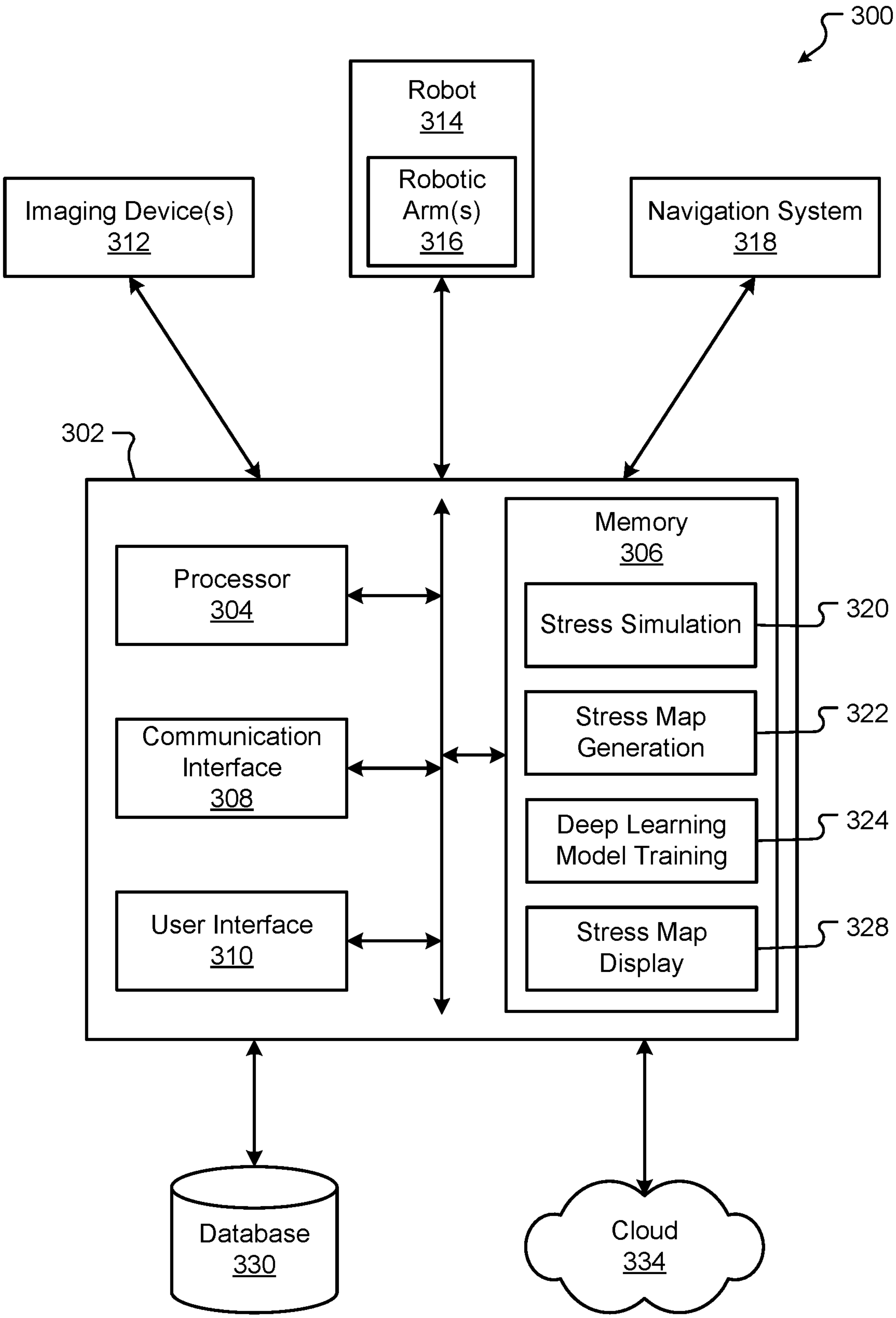
FIG. 3 is a diagram of a system according to at least one embodiment of the present disclosure.

Turning to FIG. 3, a diagram of a system 300 according to at least one embodiment of the present disclosure is shown. The system 300 may be used to generate spine stress maps based at least in part on an FE analysis, as described with reference to FIGS. 1 and 2. The system 300 comprises a computing device 302, one or more imaging devices 312, a robot 314, a navigation system 318, a database 330, and/or a cloud or other network 334. Systems according to other embodiments of the present disclosure may comprise more or fewer components than the system 300. For example, the system 300 may not include the imaging device 312, the robot 314, the navigation system 318, one or more components of the computing device 302, the database 330, and/or the cloud 334.

The computing device 302 comprises a processor 304, a memory 306, a communication interface 308, and a user interface 310. Computing devices according to other embodiments of the present disclosure may comprise more or fewer components than the computing device 302.

The processor 304 of the computing device 302 may be any processor described herein or any similar processor. For example, the processor 304 may be represented by the processor 104 as described with reference to FIG. 1. The processor 304 may be configured to execute instructions or data stored in the memory 306, which the instructions or data may cause the processor 304 to carry out one or more computing steps utilizing or based on data received from the imaging device 312, the robot 314, the navigation system 318, the database 330, and/or the cloud 334.

The memory 306 may be or comprise RAM, DRAM, SDRAM, other solid-state memory, any memory described herein, or any other tangible, non-transitory memory for storing computer-readable data and/or instructions. The memory 306 may store information or data useful for completing, for example, any step of the methods 400, 500, and/or 600 described herein, or of any other methods. The memory 306 may store, for example, instructions and/or machine learning models that support one or more functions of the robot 314. For instance, the memory 306 may store content (e.g., instructions and/or machine learning models) that, when executed by the processor 304, enable stress stimulation 320, stress map generation 322, deep learning model training 324, and/or stress map display 328.

The stress stimulation 320 enables the processor 304 to simulate stresses on an anatomical element of a patient (e.g., different elements of a spine). For example, the simulated stresses may be simulated using an FE analysis. In some embodiments, the stress stimulation 320 enables the processor 304 to simulate a plurality of stresses on the anatomical element based at least in part on simulating a plurality of physiological movements and deformations that cause stress on the anatomical element. For example, the simulated stresses may comprise moving a vertebra of the spinal cord, squeezing a disc of the spinal cord, resizing a ligamentum flavum of the spinal cord, a deformation of the spinal cord, an additional physiological movement of the spinal cord, or a combination thereof.

The stress map generation 322 enables the processor 304 to generate a plurality of stress maps and/or a multi-class segmentation for the anatomical element of the patient based at least in part on simulating the stresses on the anatomical element. For example, the stress map generation 322 enables the processor 304 to generate individual stress maps for each of the plurality of simulated stresses, where the plurality of stress maps comprises the individual stress maps. In some embodiments, the plurality of stress maps may comprise 3D stress maps of the anatomical element.

The deep learning model training 324 enables the processor 304 to train a first deep learning model based at least in part on a plurality of MR images (e.g., acquired from the imaging device(s) 312 and/or the database 330) of the anatomical element from a plurality of patients (e.g., MRI spine database), where the multi-class segmentation is generated based at least in part on the first deep learning model. In some embodiments, the first deep learning model may further be trained based at least in part on a plurality of annotated soft tissue segmentation maps for the anatomical element from the plurality of patients. Additionally, the plurality of MR images may comprise a plurality of 3D MR images.

Additionally or alternatively, the deep learning model training 324 enables the processor 304 to train a second deep learning model based at least in part on the plurality of stress maps and the multi-class segmentation for the anatomical element (e.g., outputs of the FE analysis that simulates the stresses). Subsequently, the deep learning model training 324 enables the processor 304 to generate one or more of the plurality of stress maps to display (e.g., via the user interface 310) based at least in part on the second deep learning model.

In some embodiments, the deep learning model training 324 may optionally enable the processor 304 to generate a plurality of simulated stress relief maps based at least in part on the plurality of stress maps and simulating removal of one or more portions of the anatomical element, where the one or more portions of the anatomical element are simulated being removed based at least in part on an additional FE analysis. Additionally, the deep learning model training 324 may enable the processor 304 to train the second deep learning model based at least in part on the plurality of simulated stress relief maps and to generate a suggested surgical plan based at least in part on the second deep learning model.

The stress map display 328 enables the processor 304 to display one or more of the plurality of stress maps (e.g., via a user interface 310). Additionally, the stress map display 328 may optionally enable the processor 304 to display the suggested surgical plan (e.g., via the user interface 310), where the suggested surgical plan is generated based at least in part on the plurality of simulated stress relief maps.

Content stored in the memory 306, if provided as in instruction, may, in some embodiments, be organized into one or more applications, modules, packages, layers, or engines. Alternatively or additionally, the memory 306 may store other types of content or data (e.g., machine learning models, artificial neural networks, deep neural networks, etc.) that can be processed by the processor 304 to carry out the various method and features described herein. Thus, although various contents of memory 306 may be described as instructions, it should be appreciated that functionality described herein can be achieved through use of instructions, algorithms, and/or machine learning models. The data, algorithms, and/or instructions may cause the processor 304 to manipulate data stored in the memory 306 and/or received from or via the imaging device 312, the robot 314, the database 330, and/or the cloud 334.

The computing device 302 may also comprise a communication interface 308. The communication interface 308 may be used for receiving image data or other information from an external source (such as the imaging device 312, the robot 314, the navigation system 318, the database 330, the cloud 334, and/or any other system or component not part of the system 300), and/or for transmitting instructions, images, or other information to an external system or device (e.g., another computing device 302, the imaging device 312, the robot 314, the navigation system 318, the database 330, the cloud 334, and/or any other system or component not part of the system 300). The communication interface 308 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 308 may be useful for enabling the device 302 to communicate with one or more other processors 304 or computing devices 302, whether to reduce the time needed to accomplish a computing-intensive task or for any other reason.

The computing device 302 may also comprise one or more user interfaces 310. The user interface 310 may be or comprise a keyboard, mouse, trackball, monitor, television, screen, touchscreen, and/or any other device for receiving information from a user and/or for providing information to a user. The user interface 310 may be used, for example, to receive a user selection or other user input regarding any step of any method described herein. Notwithstanding the foregoing, any required input for any step of any method described herein may be generated automatically by the system 300 (e.g., by the processor 304 or another component of the system 300) or received by the system 300 from a source external to the system 300. In some embodiments, the user interface 310 may be useful to allow a surgeon or other user to modify instructions to be executed by the processor 304 according to one or more embodiments of the present disclosure, and/or to modify or adjust a setting of other information displayed on the user interface 310 or corresponding thereto.

Although the user interface 310 is shown as part of the computing device 302, in some embodiments, the computing device 302 may utilize a user interface 310 that is housed separately from one or more remaining components of the computing device 302. In some embodiments, the user interface 310 may be located proximate one or more other components of the computing device 302, while in other embodiments, the user interface 310 may be located remotely from one or more other components of the computer device 302.

The imaging device 312 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 312, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 312 may be used to obtain first image data (e.g., a first image) at a first time, and a second imaging device 312 may be used to obtain second image data (e.g., a second image) at a second time after the first time. The imaging device 312 may be capable of taking a 2D image or a 3D image to yield the image data. The imaging device 312 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 312 suitable for obtaining images of an anatomical feature of a patient. The imaging device 312 may be contained entirely within a single housing, or may comprise a transmitter/emitter and a receiver/detector that are in separate housings or are otherwise physically separated.

In some embodiments, the imaging device 312 may comprise more than one imaging device 312. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 312 may be operable to generate a stream of image data. For example, the imaging device 312 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 314 may be any surgical robot or surgical robotic system. The robot 314 may be or comprise, for example, the Mazor X™ Stealth Edition robotic guidance system. The robot 314 may be configured to position the imaging device 312 at one or more precise position(s) and orientation(s), and/or to return the imaging device 312 to the same position(s) and orientation(s) at a later point in time. The robot 314 may additionally or alternatively be configured to manipulate a surgical tool (whether based on guidance from the navigation system 318 or not) to accomplish or to assist with a surgical task. In some embodiments, the robot 314 may be configured to hold and/or manipulate an anatomical element during or in connection with a surgical procedure. The robot 314 may comprise one or more robotic arms 316. In some embodiments, the robotic arm 316 may comprise a first robotic arm and a second robotic arm, though the robot 314 may comprise more than two robotic arms. In some embodiments, one or more of the robotic arms 316 may be used to hold and/or maneuver the imaging device 312. In embodiments where the imaging device 312 comprises two or more physically separate components (e.g., a transmitter and receiver), one robotic arm 316 may hold one such component, and another robotic arm 316 may hold another such component. Each robotic arm 316 may be positionable independently of the other robotic arm. The robotic arms 316 may be controlled in a single, shared coordinate space, or in separate coordinate spaces.

The robot 314, together with the robotic arm 316, may have, for example, one, two, three, four, five, six, seven, or more degrees of freedom. Further, the robotic arm 316 may be positioned or positionable in any pose, plane, and/or focal point. The pose includes a position and an orientation. As a result, an imaging device 312, surgical tool, or other object held by the robot 314 (or, more specifically, by the robotic arm 316) may be precisely positionable in one or more needed and specific positions and orientations.

The robotic arm(s) 316 may comprise one or more sensors that enable the processor 304 (or a processor of the robot 314) to determine a precise pose in space of the robotic arm (as well as any object or element held by or secured to the robotic arm).

In some embodiments, reference markers (e.g., navigation markers) may be placed on the robot 314 (including, e.g., on the robotic arm 316), the imaging device 312, or any other object in the surgical space. The reference markers may be tracked by the navigation system 318, and the results of the tracking may be used by the robot 314 and/or by an operator of the system 300 or any component thereof. In some embodiments, the navigation system 318 can be used to track other components of the system (e.g., imaging device 312) and the system can operate without the use of the robot 314 (e.g., with the surgeon manually manipulating the imaging device 312 and/or one or more surgical tools, based on information and/or instructions generated by the navigation system A18, for example).

The navigation system 318 may provide navigation for a surgeon and/or a surgical robot during an operation. The navigation system 318 may be any now-known or future-developed navigation system, including, for example, the Medtronic StealthStation™ S8 surgical navigation system or any successor thereof. The navigation system 318 may include one or more cameras or other sensor(s) for tracking one or more reference markers, navigated trackers, or other objects within the operating room or other room in which some or all of the system 300 is located. The one or more cameras may be optical cameras, infrared cameras, or other cameras. In some embodiments, the navigation system 318 may comprise one or more electromagnetic sensors. In various embodiments, the navigation system 318 may be used to track a position and orientation (e.g., a pose) of the imaging device 312, the robot 314 and/or robotic arm 316, and/or one or more surgical tools (or, more particularly, to track a pose of a navigated tracker attached, directly or indirectly, in fixed relation to the one or more of the foregoing). The navigation system 318 may include a display for displaying one or more images from an external source (e.g., the computing device 302, imaging device 312, or other source) or for displaying an image and/or video stream from the one or more cameras or other sensors of the navigation system 318. In some embodiments, the system 300 can operate without the use of the navigation system 318. The navigation system 318 may be configured to provide guidance to a surgeon or other user of the system 300 or a component thereof, to the robot 314, or to any other element of the system 300 regarding, for example, a pose of one or more anatomical elements, whether or not a tool is in the proper trajectory, and/or how to move a tool into the proper trajectory to carry out a surgical task according to a preoperative or other surgical plan.

In some embodiments, the robot 314, robotic arm(s) 316, and navigation system 318 may be operated based on the stress maps generated as described herein. For example, the stress maps and/or bone cut suggestions described herein may be used as inputs to determine a surgical plan to be performed by the components of the system 300.

The database 330 may store information that correlates one coordinate system to another (e.g., one or more robotic coordinate systems to a patient coordinate system and/or to a navigation coordinate system). The database 330 may additionally or alternatively store, for example, one or more surgical plans (including, for example, pose information about a target and/or image information about a patient's anatomy at and/or proximate the surgical site, for use by the robot 314, the navigation system 318, and/or a user of the computing device 302 or of the system 300); one or more images useful in connection with a surgery to be completed by or with the assistance of one or more other components of the system 300; and/or any other useful information. The database 330 may be configured to provide any such information to the computing device 302 or to any other device of the system 300 or external to the system 300, whether directly or via the cloud 334. In some embodiments, the database 330 may be or comprise part of a hospital image storage system, such as a picture archiving and communication system (PACS), a health information system (HIS), and/or another system for collecting, storing, managing, and/or transmitting electronic medical records including image data.

The cloud 334 may be or represent the Internet or any other wide area network. The computing device 302 may be connected to the cloud 334 via the communication interface 308, using a wired connection, a wireless connection, or both. In some embodiments, the computing device 302 may communicate with the database 330 and/or an external device (e.g., a computing device) via the cloud 334.

The system 300 or similar systems may be used, for example, to carry out one or more aspects of any of the methods 400, 500, and/or 600 described herein. The system 300 or similar systems may also be used for other purposes.

Figure 4:
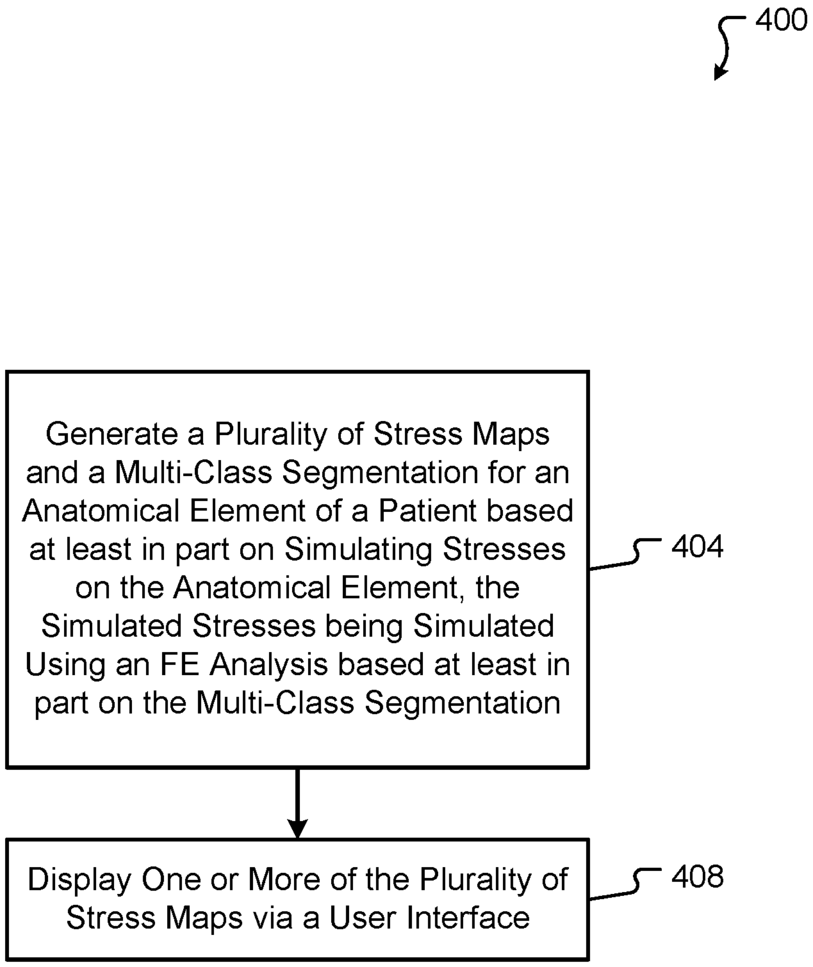
FIG. 4 is a flowchart of a method according to at least one embodiment of the present disclosure.

FIG. 4 depicts a method 400 that may be used, for example, to generate and display one or more stress maps based in part on an FE analysis.

The method 400 (and/or one or more steps thereof) may be carried out or otherwise performed, for example, by at least one processor. The at least one processor may be the same as or similar to the processor(s) 304 of the computing device 302 described above. The at least one processor may be part of a robot (such as a robot 314) or part of a navigation system (such as a navigation system 318). A processor other than any processor described herein may also be used to execute the method 400. The at least one processor may perform the method 400 by executing elements stored in a memory such as the memory 306. The elements stored in the memory and executed by the processor may cause the processor to execute one or more steps of a function as shown in method 400. One or more portions of a method 400 may be performed by the processor executing any of the contents of memory, such as a stress stimulation 320, a stress map generation 322, a deep learning model training 324, and/or a stress map display 328.

The method 400 comprises generating a multi-class segmentation for an anatomical element of a patient based at least in part on a plurality of magnetic resonance images of the anatomical element from a plurality of patients. Additionally, the method 400 comprises generating a plurality of stress maps based at least in part on simulating stresses on the anatomical element, the simulated stresses being simulated using an FE analysis based at least in part on the multi-class segmentation (step 404). For example, a plurality of stresses may be simulated on the anatomical element based at least in part on simulating a plurality of physiological movements, deformations, and/or material changes that cause stress on the anatomical element. In some embodiments, the simulated stresses may comprise moving a vertebra of the spinal cord, squeezing a disc of the spinal cord, resizing a ligamentum flavum of the spinal cord, a deformation of the spinal cord, an additional physiological movement of the spinal cord, or a combination thereof. Additionally, individual stress maps may be generated for each of the plurality of simulated stresses, where the plurality of stress maps comprises the individual stress maps. In some embodiments, the plurality of stress maps may comprise 3D stress maps of the anatomical element.

The method 400 also comprises displaying one or more of the plurality of stress maps via a user interface (step 408).

The present disclosure encompasses embodiments of the method 400 that comprise more or fewer steps than those described above, and/or one or more steps that are different than the steps described above.

Figure 5:
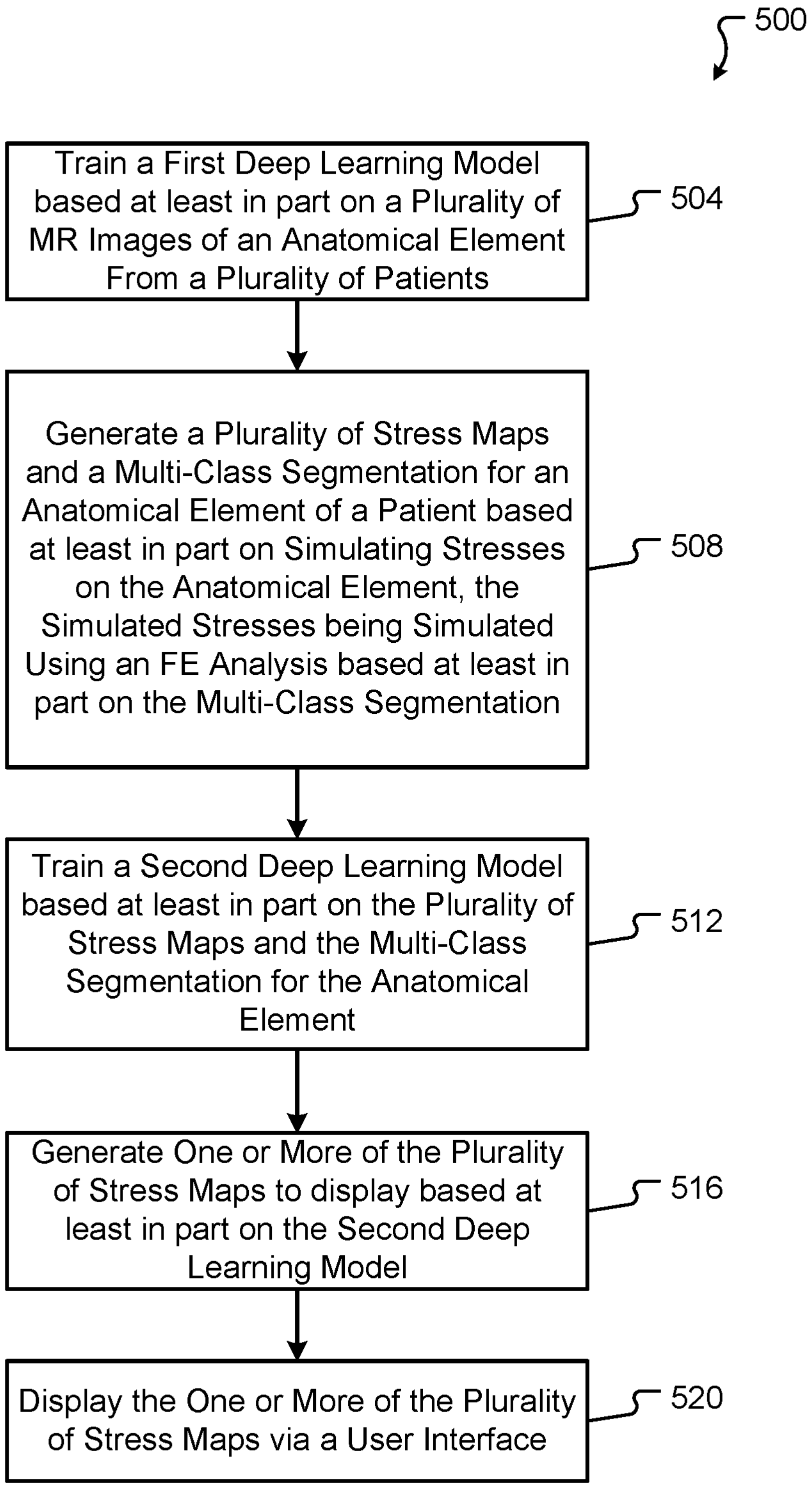
FIG. 5 is a flowchart of a method according to at least one embodiment of the present disclosure.

FIG. 5 depicts a method 500 that may be used, for example, to generate and display one or more stress maps based in part on an FE analysis and one or more deep learning models.

The method 500 (and/or one or more steps thereof) may be carried out or otherwise performed, for example, by at least one processor. The at least one processor may be the same as or similar to the processor(s) 304 of the computing device 302 described above. The at least one processor may be part of a robot (such as a robot 314) or part of a navigation system (such as a navigation system 318). A processor other than any processor described herein may also be used to execute the method 500. The at least one processor may perform the method 500 by executing elements stored in a memory such as the memory 306. The elements stored in memory and executed by the processor may cause the processor to execute one or more steps of a function as shown in method 500. One or more portions of a method 500 may be performed by the processor executing any of the contents of memory, such as a stress stimulation 320, a stress map generation 322, a deep learning model training 324, and/or a stress map display 328.

The method 500 comprises training a first deep learning model based at least in part on a plurality of MR images of an anatomical element from a plurality of patients (step 504). For example, the plurality of MR images may comprise a plurality of 3D MR images (e.g., from an MRI spine database of "good" and "bad" spines, as described with reference to FIGS. 1 and 2). In some embodiments, the first deep learning model may further be trained based at least in part on a plurality of annotated soft tissue segmentation maps for the anatomical element from the plurality of patients.

The method 500 also comprises generating a multi-class segmentation for an anatomical element of a patient based at least in part on the plurality of MR images of the anatomical element from the plurality of patients. Additionally, the method 500 comprises generating a plurality of stress maps simulating stresses on the anatomical element, the simulated stresses being simulated using an FE analysis based at least in part on the multi-class segmentation (step 508). Step 508 may implement similar aspect of step 404 as described with reference to FIG. 4. Additionally, the multi-class segmentation may be generated based at least in part on the first deep learning model.

The method 500 also comprises training a second deep learning model based at least in part on the plurality of stress maps and the multi-class segmentation for the anatomical element (step 512). The method 500 also comprises generating one or more of the plurality of stress maps to display based at least in part on the second deep learning model (step 516).

The method 500 also comprises displaying the one or more of the plurality of stress maps (e.g., generated in step 516) via a user interface (step 520).

The present disclosure encompasses embodiments of the method 500 that comprise more or fewer steps than those described above, and/or one or more steps that are different than the steps described above.

Figure 6:
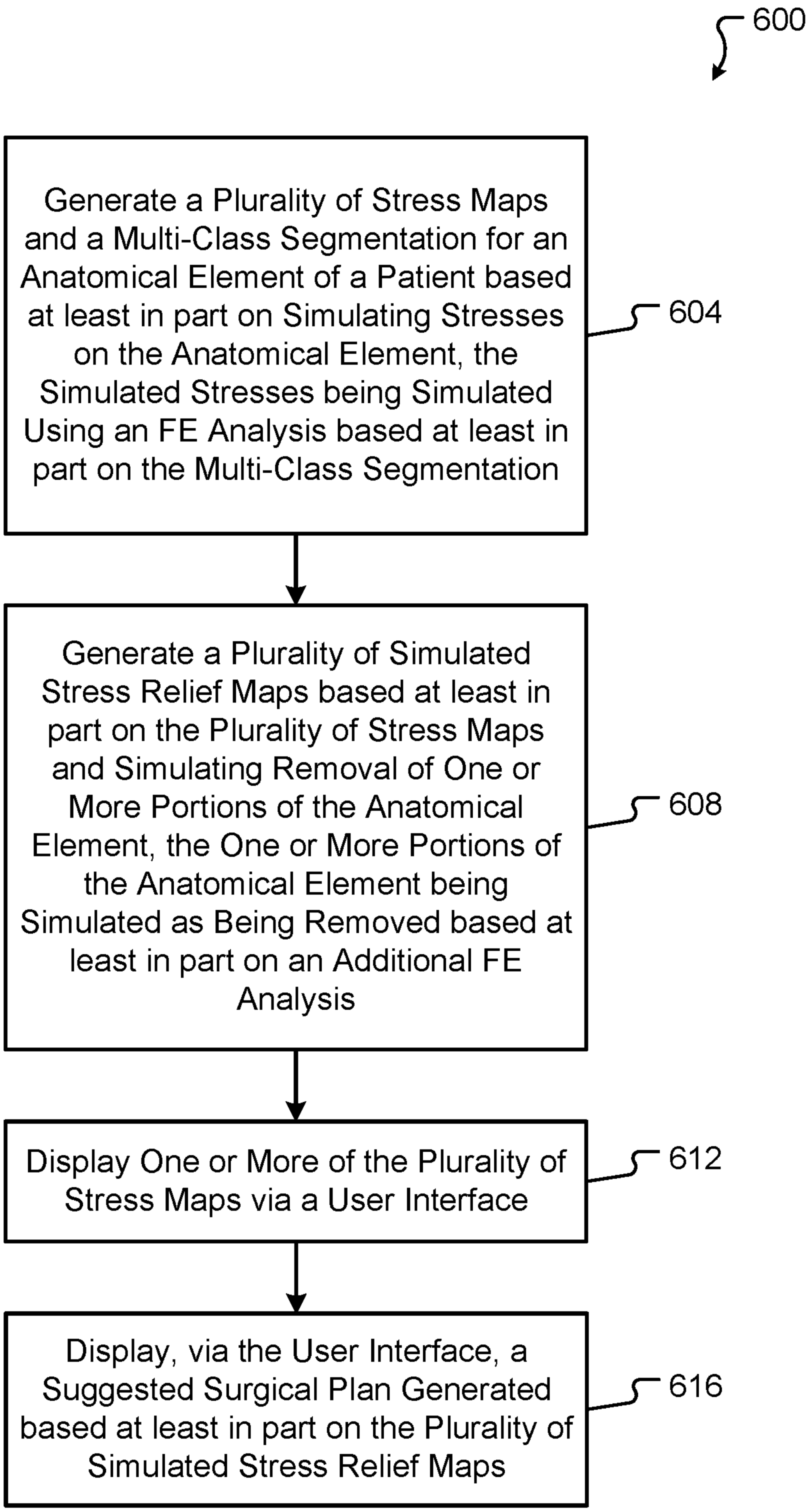
FIG. 6 is a flowchart of a method according to at least one embodiment of the present disclosure.

FIG. 6 depicts a method 600 that may be used, for example, to generate a bone cut suggestion.

The method 600 (and/or one or more steps thereof) may be carried out or otherwise performed, for example, by at least one processor. The at least one processor may be the same as or similar to the processor(s) 304 of the computing device 302 described above. The at least one processor may be part of a robot (such as a robot 314) or part of a navigation system (such as a navigation system 318). A processor other than any processor described herein may also be used to execute the method 600. The at least one processor may perform the method 600 by executing elements stored in a memory such as the memory 306. The elements stored in memory and executed by the processor may cause the processor to execute one or more steps of a function as shown in method 600. One or more portions of a method 600 may be performed by the processor executing any of the contents of memory, such as a stress stimulation 320, a stress map generation 322, a deep learning model training 324, and/or a stress map display 328.

The method 600 comprises generating a plurality of stress maps and a multi-class segmentation for an anatomical element of a patient based at least in part on simulating stresses on the anatomical element, the simulated stresses being simulated using an FE analysis based at least in part on the multi-class segmentation (step 604). Step 604 may implement similar aspect of steps 404 and 508 as described with reference to FIGS. 4 and 5, respectively.

The method 600 also comprises generating a plurality of simulated stress relief maps based at least in part on the plurality of stress maps and simulating removal of one or more portions of the anatomical element, where the one or more portions of the anatomical element are simulated being removed based at least in part on an additional FE analysis (step 608). In some embodiments, a deep learning model (e.g., the second deep learning model described herein or an additional deep learning model) is trained based at least in part on the plurality of simulated stress relief maps, and a suggested surgical plan may be generated based at least in part on the deep learning model. For example, the suggested surgical plan may comprise a bone cut suggestion or recommendation.

The method 600 also comprises displaying one or more of the plurality of stress maps (via a user interface (step 612). The method 600 also comprises displaying the suggested surgical plan via the user interface based at least in part on the plurality of simulated stress relief maps (step 616).

The present disclosure encompasses embodiments of the method 600 that comprise more or fewer steps than those described above, and/or one or more steps that are different than the steps described above.

As noted above, the present disclosure encompasses methods with fewer than all of the steps identified in FIGS. 4, 5, and 6 (and the corresponding description of the methods 400, 500, and 600), as well as methods that include additional steps beyond those identified in FIGS. 4, 5, and 6 (and the corresponding description of the methods 400, 500, and 600). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for creating a spine stress map, comprising:
a processor; and
a memory storing data for processing by the processor, the data, when processed, causes the processor to:
generate a multi-class segmentation for an anatomical element of a patient based at least in part on a plurality of magnetic resonance images of the anatomical element from a plurality of patients;
generate a plurality of stress maps based at least in part on simulating stresses on the anatomical element, the simulated stresses being simulated using a finite element analysis based at least in part on the multi-class segmentation;
determine one or more stress maps of the plurality of stress maps to display based at least in part on one or more deep learning models configured to predict multi-labeled masks and/or stress maps for the anatomical element;
generate a plurality of simulated stress relief maps based at least in part on the plurality of stress maps and simulating removal of one or more portions of the anatomical element, wherein the one or more portions of the anatomical element are simulated being removed based at least in part on an additional finite element analysis; and
display at least one of the one or more stress maps and/or a suggested surgical plan generated based at least in part on the plurality of simulated stress relief maps via a user interface.

2. The system of claim 1, wherein the memory stores further data for processing by the processor that, when processed, causes the processor to:
train a deep learning model based at least in part on the plurality of magnetic resonance images of the anatomical element from the plurality of patients; and
generate the multi-class segmentation based at least in part on the deep learning model.

3. The system of claim 2, wherein the deep learning model is further trained based at least in part on a plurality of annotated soft tissue segmentation maps for the anatomical element from the plurality of patients.

4. The system of claim 2, wherein the plurality of magnetic resonance images comprises a plurality of three-dimensional magnetic resonance images.

5. The system of claim 1, wherein the memory stores further data for processing by the processor that, when processed, causes the processor to:
simulate a plurality of stresses on the anatomical element based at least in part on simulating a plurality of physiological movements, deformations, material changes, or a combination thereof that cause stress on the anatomical element.

6. The system of claim 5, wherein the memory stores further data for processing by the processor that, when processed, causes the processor to:
generate individual stress maps for each of the plurality of simulated stresses, wherein the plurality of stress maps comprises the individual stress maps.

7. The system of claim 1, wherein the memory stores further data for processing by the processor that, when processed, causes the processor to:
train a deep learning model based at least in part on the plurality of stress maps and the multi-class segmentation for the anatomical element; and
generate the one or more stress maps to display via the user interface based at least in part on the deep learning model.

8. The system of claim 1, wherein the memory stores further data for processing by the processor that, when processed, causes the processor to:
train a deep learning model based at least in part on the plurality of simulated stress relief maps, wherein the suggested surgical plan is generated based at least in part on the deep learning model.

9. The system of claim 1, wherein the plurality of stress maps comprises three-dimensional stress maps of the anatomical element.

10. A system for creating a spine stress map, comprising:
a processor; and
a memory storing data for processing by the processor, the data, when processed, causes the processor to:
generate a multi-class segmentation for an anatomical element of a patient based at least in part on a plurality of magnetic resonance images of an anatomical element from a plurality of patients;
generate a plurality of stress maps for the anatomical element of a patient based at least in part on simulating stresses on the multi-class segmentation of the anatomical element, the simulated stresses being simulated using a finite element analysis based at least in part on the multi-class segmentation;
determine one or more stress maps of the plurality of stress maps to display based at least in part on a deep learning model configured to predict multi-labeled masks and/or stress maps for the anatomical element;
generate a plurality of simulated stress relief maps based at least in part on the plurality of stress maps and simulating removal of one or more portions of the anatomical element, wherein the one or more portions of the anatomical element are simulated being removed based at least in part on an additional finite element analysis; and
display one or more of the plurality of stress maps and/or a suggested surgical plan generated based at least in part on the plurality of simulated stress relief maps via a user interface.

11. The system of claim 10, wherein the memory stores further data for processing by the processor that, when processed, causes the processor to:
train a first deep learning model based at least in part on the plurality of magnetic resonance images of the anatomical element from the plurality of patients; and
generate the multi-class segmentation based at least in part on the first deep learning model.

12. The system of claim 11, wherein the memory stores further data for processing by the processor that, when processed, causes the processor to:

train a second deep learning model based at least in part on the plurality of stress maps and the multi-class segmentation for the anatomical element; and generate the one or more of the plurality of stress maps to display via the user interface based at least in part on the deep learning model.

13. The system of claim 11, wherein the first deep learning model is further trained based at least in part on a plurality of annotated soft tissue segmentation maps for the anatomical element from the plurality of patients.

14. The system of claim 10, wherein the memory stores further data for processing by the processor that, when processed, causes the processor to:

simulate a plurality of stresses on the anatomical element based at least in part on simulating a plurality of physiological movements, deformations, material changes, or a combination thereof that cause stress on the anatomical element.

15. The system of claim 14, wherein the memory stores further data for processing by the processor that, when processed, causes the processor to:

generate individual stress maps for each of the plurality of simulated stresses, wherein the plurality of stress maps comprises the individual stress maps.

16. The system of claim 10, wherein the memory stores further data for processing by the processor that, when processed, causes the processor to:

train a deep learning model based at least in part on the plurality of simulated stress relief maps, wherein the suggested surgical plan is generated based at least in part on the deep learning model.

17. A system for creating a spine stress map, comprising:

a processor; and a memory storing data for processing by the processor, the data, when processed, causes the processor to:

generate a multi-class segmentation for a spinal cord of a patient based at least in part on a plurality of magnetic resonance images of spinal cords from a plurality of patients;

generate a plurality of stress maps based at least in part on simulating stresses on the spinal cord, the simulated stresses being simulated using a finite element analysis based at least in part on the multi-class segmentation;

determine one or more stress maps of the plurality of stress maps to display based at least in part on one or more deep learning models configured to predict multi-labeled masks and/or stress maps for the spinal cord;

generate a plurality of simulated stress relief maps based at least in part on the plurality of stress maps and simulating removal of one or more portions of the spinal cord, wherein the one or more portions of the spinal cord are simulated being removed based at least in part on an additional finite element analysis; and display one or more of the plurality of stress maps and/or a suggested surgical plan generated based at least in part on the plurality of simulated stress relief maps via a user interface.

18. The system of claim 17, wherein the simulated stresses comprise moving a vertebra of the spinal cord, squeezing a disc of the spinal cord, resizing a ligamentum flavum of the spinal cord, a deformation of the spinal cord, an additional physiological movement of the spinal cord, or a combination thereof.

* * * * *